US008486388B2

(12) United States Patent
Jezek

(10) Patent No.: US 8,486,388 B2
(45) Date of Patent: Jul. 16, 2013

(54) PROTEIN FORMULATION

(75) Inventor: Jan Jezek, Wellingborough (GB)

(73) Assignee: Arecor Limited, Cambridge (GB)

(*) Notice: Subject to any disclaimer, the term of this patent is extended or adjusted under 35 U.S.C. 154(b) by 0 days.

(21) Appl. No.: 12/913,838

(22) Filed: Oct. 28, 2010

(65) Prior Publication Data

US 2011/0171264 A1 Jul. 14, 2011

Related U.S. Application Data

(63) Continuation of application No. PCT/EP2009/055317, filed on May 1, 2009.

(30) Foreign Application Priority Data

May 1, 2008 (EP) .................................... 08155538

(51) Int. Cl.
*A61K 38/54* (2006.01)

(52) U.S. Cl.
USPC ........................................................ 424/94.3

(58) Field of Classification Search
USPC ...................... 424/94.4, 246.1; 514/1.1, 14.1
See application file for complete search history.

(56) References Cited

U.S. PATENT DOCUMENTS

| | | | |
|---|---|---|---|
| 5,919,766 | A | 7/1999 | Österberg et al. |
| 2004/0116345 | A1 | 6/2004 | Besman et al. |
| 2009/0136538 | A1 | 5/2009 | Jezek |
| 2010/0028372 | A1 | 2/2010 | Jezek |

FOREIGN PATENT DOCUMENTS

| | | | |
|---|---|---|---|
| EP | 0 340 068 | A1 | 11/1989 |
| EP | 1 716 865 | A1 | 11/2006 |
| WO | 94/26286 | A1 | 11/1994 |
| WO | 96/30041 | A1 | 10/1996 |
| WO | WO 0103727 | A1 * | 1/2001 |
| WO | 03/080108 | A1 | 10/2003 |
| WO | 2006/009989 | A1 | 1/2006 |
| WO | 2007/003936 | A1 | 1/2007 |
| WO | 2007/109221 | A2 | 9/2007 |
| WO | 2007/135425 | A1 | 11/2007 |
| WO | 2008/084237 | A2 | 7/2008 |

OTHER PUBLICATIONS

Petosa et al., Crystal structure of the anthrax toxin protective antigen, 1997, Nature, 385(6619): 833-8.*
Klimpel et al., Anthrax toxin protective antigen is activated by a cell surface protease with the sequence specificity and catalytic properties of furin, 1992, Proc. Natl. Acad. Sci. USA., 89: 10277-81.*
Wakabayashi et al., Residues 110-126 in the A1 domain of factor VIII contain a Ca2+ binding site required for cofactor activity, 2004, J. Biol. Chem., 279(13): 12677-84.*
Blanchard et al., Buffers for enzymes, 1984, Methods Enzymol. 104: 404-14.*
Sekiya et al., Regulation of the tertiary structure and function of coagulation factor IX by magnesium (II) ions, 1995, Journal of Biological Chemistry 270(24): 14325-14331.*
International Search Report for PCT/EP2009/055317, dated Aug. 11, 2009.
Smith, A. T., et al., "Expression of a Synthetic Gene for Horseradish Peroxidase C in *Escherichia coli* and Folding and Activation of the Recombinant Enzyme with Ca2+ and Heme*," The Journal of Biological Chemistry, 265(22): 13335-13343 (1990).
Josic, D., et al., "Purification of Factor VIII and Von Willebrand Factor from Human Plasma by Anion-Exchange Chromatography," J. Chromatography, 662(2): 181-190 (1994).
Gwinn, W., et al., "Scalable purification of *Bacillus anthracis* protective antigen from *Escherichia coli*," Protein Expression and Purification, 45: 30-36 (2006).
Shi, X., et al., "Overexpression, purification, and characterization of a recombinant secretary catalase from *Bacillus subtilis*," Biotechnol Lett, 30: 181-186 (2008).
Wilson, C. J., et al., XP0091 03220, "Role of cofactors in metalloprotein folding," Quarterly Review of Biophysics, 37 (3/4): 285-314 (2004).
McIntosh, R. V., et al., "The Effect of Solution Formulation on the Stability and Surface Interactions of Factor VIII During Plasma Fractionation," Transfus, Sci., 11(1): 55-66 (1990).

* cited by examiner

*Primary Examiner* — Jon P Weber
*Assistant Examiner* — Robert Yamasaki
(74) *Attorney, Agent, or Firm* — Sterne, Kessler, Goldstein & Fox P.L.L.C.

(57) ABSTRACT

An aqueous composition which comprises a protein or other biological molecule and also (i) optionally comprises one or more metal ions at a concentration of 0.01 to 20 mM; (ii) comprises excipients which are weak ligands; and (iii) is substantially free of excipients which are medium-strength ligands, and is substantially free of excipients which are strong ligands in free form.

21 Claims, No Drawings

PROTEIN FORMULATION

RELATED APPLICATION

This application is a continuation of International Application No. PCT/EP2009/055317, which designated the United States and was filed on May 1, 2009, published in English. This application claims priority under 35 U.S.C. §119 or 365 to European Application No. 08155538.5, filed on May 1, 2008. The entire teachings of the above applications are incorporated herein by reference.

FIELD OF THE INVENTION

This invention relates to the stability of proteins and other biological molecules and supramolecular systems, in particular to the stability of such molecules which can bind metal ions, such as calcium ion, in their three-dimensional structure, particularly the stability of such proteins in aqueous systems, for example in aqueous solution, in aqueous gel form or in non-liquid state such as solid state where free or bound water is present, e.g. in frozen condition or following partial removal of water such as by drying or freeze-drying.

BACKGROUND OF THE INVENTION

Many biological molecules and supramolecular systems, for example proteins, virus-like particles or attenuated viruses, are unstable and are susceptible to structural degradation and consequent loss of activity while stored, particularly in aqueous solutions. The processes involved in protein degradation can be divided into physical (i.e. processes affecting non-covalent interactions, such as loss of quaternary, tertiary or secondary structure, aggregation, surface adsorption) and chemical (i.e. processes involving a covalent change such as de-amidation, oxidation, disulphide scrambling etc.). The rates of the degradation processes are typically proportional to temperature. Biological molecules and supramolecular systems are therefore generally more stable at lower temperatures.

Metalloproteins are a class of proteins that contain one or more metal ions in their structure. The metal ion may be a part of a more complex chemical component (e.g. haem) which is bound within the protein structure. Alternatively, the metal ion may be bound directly to one or more amino acid side chains within the structure of the protein via various non-covalent interactions (co-ordinate interactions, hydrogen bonds, charge-charge interactions etc.). Whilst in some cases the metal may be essential for the protein's biological activity, in other cases it only plays a structural role. Whilst in some cases, for example in the Factor VIII molecule, the metal forms a bridge between two protein subunits, in other cases, for example in recombinant Anthrax protective antigen, the metal is confined within one subunit. The loss of the metal from the protein structure is likely to affect the function and/or the structure of the protein. Depending on the position of the metal within the protein molecule, the loss of the metal can lead to physical separation of key domains or to conformational change within one domain. Therefore, in order to maintain the native structure of the protein, it is very important to keep the protein in a formulation in which the binding interactions between the metal and the amino acid structure of the protein are maintained optimally.

SUMMARY OF THE INVENTION

The present invention is based on the discovery of several desirable aspects of formulations of proteins and other biological molecules and supramolecular systems, in particular to the stability of such molecules proteins which can bind metal ions, such as calcium ion, in their three-dimensional structure. Implementation of some or all of these aspects results in a considerable stabilisation of those molecules during storage.

In some aspects, the present invention addresses optimal formulations of metalloproteins. However, the invention is not limited to metalloproteins and can be used with any biological molecule or supramolecular system.

DESCRIPTION OF THE INVENTION

There are several subclasses of metalloproteins. A major subclass are proteins that contain calcium ion ($Ca^{2+}$) in their tertiary structure. These proteins have often important biological functions. Examples of commercially important calcium-containing proteins include some of the blood factors involved in the blood coagulation cascade (e.g. Factor VIII, Factor VIIa), various glucosidases, recombinant Anthrax protective antigen (rPA), some peroxidases etc. Another subclass of metalloproteins are haem-containing proteins, such as catalase or peroxidase. In these cases the metal (iron) is bound within a more complex structure (haem), which, in turn is bound within the tertiary structure of the protein. Various other metals can be an essential part of the protein structure, such as zinc, copper or magnesium.

The exact details of the interactions between the metal ions and amino acid residues within the tertiary structure of a protein can be obtained very easily from various resources available in the public domain, such as the Protein Data Bank (http://pdbbeta.rcsb.org/pdb/home/home.do). So, for example, the following information can be obtained from the Protein data bank web source in relation to the recombinant Anthrax protective antigen (Petosa et al.: Anthrax protective antigen; code 1ACC): Each molecule of rPA contains two calcium ions. The calcium ions are bound to several amino acid side chains within one of the four domains of the rPA molecule. The binding interactions are of non-covalent nature and include bridged hydrogen bonds, charge-charge interactions and co-ordinate interactions. Interactions of calcium ions with the following amino acids side chains within the rPA domain have been identified: Asp177, Asp179, Asn180, Asp181, Asp185, Glu188, Ser222, Glu224, Lys225 and Asp235. The amino acids with carboxylic groups in their side chains, i.e. Aspartate (Asp) or Glutamate (Glu), appear to be particularly effective in forming binding interactions with calcium ion within the protein structures due to their charge and a number of available free pairs of electrons.

A typical formulation of a biological molecule or supramolecular system (e.g. a therapeutic protein or a vaccine) contains a buffer (for example phosphate or citrate) and typically one or more of the following components: tonicity modifiers (typically inorganic salts or amino acids), surfactants (for example Polysorbate 80) and sugars or polyalcohols (for example sucrose). Some commercial formulations of calcium-containing proteins comprise calcium cation, typically in the form of calcium chloride. So, for example, Kongenate, one of the commercially available recombinant factor VIII products, contains 2-3 mM calcium chloride, together with histidine (18-23 mM), glycylglycine (21-25 g/L), sucrose (0.9-1.3%) and polysorbate 80 (35 μg/mL). This example demonstrates that the importance of the presence of metal cation in the formulation of a protein which contains the same cation in its structure is generally appreciated.

Almost every compound that can be considered as an excipient in a protein formulation has some degree of the ability to bind metals resulting in formation of complex ions. Such complex ions consist of a metal ion in the centre and one or more other molecules surrounding it. The molecules surrounding the central metal ion are called ligands. The formation of the complex ion between metal ion and ligands can be best explained by the Lewis theory of acids and bases. All ligands contain at least one lone pair of electrons and are therefore Lewis bases. All metal cations contain empty electron orbitals in their outer electron layers and are therefore Lewis acids. The energy of these orbitals can be lowered by accepting one or more lone pairs of electrons from other molecules (ligands), which leads to energetically more stable systems. The system has lowest energy (and is therefore most stable) if all available empty orbitals of the metal cation are filled with electrons from the lone electron pairs of the ligand(s). The bond between a metal ion and a ligand is referred to as co-ordinate bond. Some ligands have only one lone pair of electrons capable of forming a bond with the central metal ion. Such ligands are said to be unidentate. In many cases, the central metal ion is surrounded by several unidentate ligands. However, some ligands have such a distribution of lone pairs of electrons in their molecules that they can form two or more co-ordinate bonds with the central metal ion and are called polydentate (bidentate, tridentate, etc.). So, 1,2-diaminoethane is an example of a bidentate ligand, haem is an example of a tetradentate ligand and EDTA of a hexadentate ligand. The complex ions involving polydentate ligands are referred to as chelates. Chelates are more stable than complexes involving monodentate ligands, the stability (i.e. the overall metal-binding strength of the ligand) increasing with the number of lone pairs of electrons that one ligand molecule can engage in the chelate formation. For this reason, a metal surrounded by six monodentate ligands is bound significantly less strongly than being chelated by one hexadentate ligand.

The bond between a metal and a ligand follows the principles of a dynamic chemical equilibrium, and can therefore be described by equilibrium constants, sometimes called "stability constants" as follows (M=metal, L=ligand):

$$M + L \rightleftharpoons M - L$$
$$K = \frac{[M - L]}{[M][L]}$$

In those cases where more than one ligand molecule can bind to the central metal ion the equilibrium is described by a series of equilibrium constants:

$$K_1 = \frac{[M - L]}{[M][L]}$$
$$K_2 = \frac{[M - L_2]}{[M - L][L]}$$
$$K_3 = \frac{[M - L_3]}{[M - L_2][L]}$$
Etc.

Alternatively, an overall stability constant can be used to quantify the binding ability of polydentate ligands as follows:

$$K = \frac{[M - L_x]}{[M][L]}$$

where [M–L$_x$] is the overall concentration of the various forms of metal-ligand complex, [M] is the concentration of free metal and [L] is the concentration of free ligand. As the values of stability constants are often very high they are typically expressed as a 10-base logarithm (log K).

The overall stability constants of metal-ligand complexes can be obtained from a comprehensive database published by the US National Institute of Standards and Technology (NIST Standard Reference Database 46, R. M. Smith and A. E. Martell: Critically Selected Stability Constants of Metal Complexes Database). This database lists over 49,000 stability constants involving 6,173 ligands and 216 metal ions in various oxidation states. One skilled in the art will be able to calculate the concentration of free metal and the concentration of metal bound in the complex from the stability constants provided that the overall (i.e. bound+unbound) concentration of the metal in the system and the overall (i.e. bound+unbound) concentration of the ligands in the system are known.

The log K values range from about 0 to >15. For a particular metal, the log K values will be lowest for monodentate ligands and increase with the number of lone pairs of electrons that a ligand can engage in the co-ordinate bond (bidentate, tri-dentate etc.). However, the log K values are also very dependent on the metal and the number of vacant electron orbitals in outer electron layers. So, for example, the log K of the complex between copper and histidine is 10.16 whilst the complex between calcium and histidine has log K value of only 1.21. Similarly, the log K of the complex between copper and EDTA is 18.78 whilst the log K of the complex between calcium and EDTA is 10.81.

Ligands with high log K will bind majority of metal ions in the system providing their concentration is equal or higher than that of the metal. If the concentration of the ligands with high log K is lower than that of the metal they will exist predominantly in the form of the metal-ligand complex and the concentration of the free ligand will be minimal. Importantly, however, even ligands with relatively low log K, such as between 1 to 2, are still very efficient in binding the metal ion. So, for example a ligand with log K=2 at a concentration twice higher than the concentration of a metal ion will bind >99% of the metal.

In most aqueous systems there will be a number of ligands competing for binding a metal. In equilibrium, some of the metal ions will be free (i.e. unbound) whilst some will be bound to various ligands. The equilibrium concentration of all species can be determined if the total concentration of the metal, the total concentration of each ligand and the stability constants of all complexes involved are known. One skilled in the art will be able to calculate the concentrations of free metal and the concentration of all metal complexes in the system from the stability constants and the overall concentration of the metal in the system and the overall concentration of all ligands in the system. As a rule of thumb, if the difference between the log K of two ligands is >1 then the metal ions will be predominantly complexed by the ligand with higher log K and binding to the ligand with lower log K will only become significant if the metal concentration exceeds that of the stronger ligand.

The equilibrium between metal-ligand complexes, free metal ions and free ligands is a dynamic process. So, whilst the concentrations of all species in the system are maintained constant in equilibrium, the metal ions will be continuously exchanged between the ligands. Similarly, there will be a continuous exchange between the free metal ions and those bound with the ligands. Exchange of metal ions between ligands with similar stability constants will occur more readily than between ligands with very different stability constants. Similarly, the metal exchange will occur more readily between the free metal and one bound with a ligand with low stability constant compared with that of a ligand with high stability constant.

There are numerous sites within the structure of any biological molecule, such as a protein or a virus, that are capable of forming a co-ordinate bond with a metal ion. So, the biological molecule will form various complexes with metal ions present in the formulation. Such complexes can be detrimental as they may facilitate aggregation of the biological molecules by forming a bridge between two molecules. Metal ions capable of forming very strong co-ordinate bonds with side chains of amino acids or other surface components of the biological molecules, such as copper or zinc, are particularly efficient in promoting aggregation whilst metals that form weaker complexes with the side chains of amino acids, such as calcium ion, are less likely to contribute to the protein aggregation. So, for example, the presence of 0.2 mM $Cu^{2+}$ or $Zn^{2+}$ was found to result in a rapid aggregation of human growth hormone at room temperature, whilst the presence of $Ca^{2+}$ had a negligible effect even at 2 mM concentration.

In addition, some metals, such as copper or iron, may catalyse oxidative processes in aqueous formulations, especially in the presence of UV light, thus further contributing to the degradation of biological molecules. Consequently, it is often desirable to remove metals from the formulation of biological molecules.

However, various biological molecules, especially those whose function and/or structure is dependent on a particular metal ion, may benefit from the presence of such metal ion in the formulation. In such cases it is important to create an optimal balance of metal ions in the formulation so that the essential metal ion is present whilst the metal-facilitated aggregation is reduced to minimum. The present invention addresses such formulations.

Nearly all compounds used in conventional formulations of biological molecules, especially biological molecules used in therapeutic applications, have some degree of the ability to bind metals resulting in formation of complex ions. Such processes are very likely to compromise stability of those biological molecules whose structure is to some extent dependent on appropriate binding of a metal ion, by interfering with co-ordinate bonds between the biological molecule and the metal.

The dynamic principles of metal-ligand bonds, as explained above, apply also to metals bound within the structure of a protein or another biological molecule. The dynamic equilibrium governing the interactions between biological molecules, metal ions and excipients present in the formulation is explained below using proteins as an typical example of biological molecules. However, the same principles apply to any other biological molecule or a supramolecular system, such as nucleic acids, virus-like particles or whole viruses.

There is a continuous competition for the metal between the binding site of the protein and other ligands present in the formulation providing the ligands can access the binding site of the metal within the protein structure. The accessibility of the metal ion within the protein structure may be restricted for some ligands due to their charge and/or size, especially if the metal is located deep inside the protein structure.

If binding of a metal within the protein structure is beneficial for its function and/or structure then it is important to minimise the competition for metal binding by ligands present in the formulation in order to reduce the rate of the metal ion loss from the structure of the protein and consequent denaturation. To some extent this can be achieved by adding a source of the metal ion into the protein formulation. The added metal ions then occupy the ligands which are, in turn, less likely to interfere with the metal bound within the protein. However, it is equally important to reduce the power of the ligands surrounding the protein to bind the key metal ion. This can be achieved by (a) selecting compounds in the protein formulation (e.g. buffers or tonicity modifiers) with very low stability constants (i.e. log K) and (b) by keeping their concentration to a minimum. Whilst the need to avoid very strong complexing agents, i.e. compounds with extremely high stability constants (such as EDTA) in formulations of such proteins may be generally appreciated, the effect of ligands with considerably lower stability constant may be underestimated. However, due to the dynamic principles of the metal binding there is some probability that even a compound with a relatively low stability constant will be competing for metal binding. Whilst the compounds with lower stability constant will not be as efficient as strong complexing agents in competing for the metal binding they will still contribute to the competition over a long period of time (e.g. during storage of the protein).

The importance of the dynamic aspect of the metal-ligand equilibrium in the protein formulation and the consequent contribution of excipients with relatively low stability constants to the competition for metal binding may have been underestimated so far, and is addressed in this invention.

Importantly, it is only the free form of the ligand, i.e. a molecule of the ligand which is not bound to a metal ion at the particular point of time, that can engage in competition for a metal ion binding. The concentration of the free form of ligand depends on the total concentration of the ligand and the total concentration of metal ions in the system. So, if there are no metal ions present in the system then the concentration of the free form of a ligand equals the total concentration of the ligand. In the presence of metal ions in the system the concentration of the free form of a ligand will always be lower than the total ligand concentration, because a portion of the ligand will be bound to the metal.

In the context of the present invention, it is important to realise that, if the concentration of metal ion(s) in the system is greater than the concentration of a very strong complexing agent (i.e. ligand with very high stability constant), then the concentration of the free form of this ligand is negligible. In contrast, if the stability constant of the ligand is relatively low then the concentration of the free form of the ligand will be higher, in such system. This can be demonstrated in the following example:

system 1 comprises 5 mM calcium ion and 4 mM EDTA (a strong complexing agent, log K=10.81);

system 2 comprises 5 mM calcium ion and 4 mM histidine (a mild complexing agent, log K=1.21);

system 3 comprises 5 mM calcium ion, 4 mM EDTA and 4 mM histidine.

The equilibrium concentrations of the free forms of the ligands are as follows:

in system 1 the concentration of free EDTA is $6.2 \times 10^{-11}$ mM;

in system 2 the concentration of free histidine is 0.197 mM;

in system 3 the concentration of free EDTA is $6.2 \times 10^{-11}$ mM and the concentration of free histidine is 3.02 mM.

The above example demonstrates that the ability of a ligand to compete in binding of a metal within protein structure depends not only on the log K value of this ligand, but also on the presence of other components in the system. So, whilst EDTA is a very strong complexing agent its ability to compete for a metal binding within the protein structure in system 1 or system 3 is negligible due to the very low concentration of its free form. The ability of histidine to compete for metal binding within protein structure in system 2 or system 3 may be higher due to the more meaningful concentration of its free form. This is in spite of the fact that histidine is a considerably weaker complexing agent. These principles are important in some aspects of the present invention.

Some compounds used in the conventional protein formulations can precipitate various metal ions. For example, calcium ion, one of the most common metal ions bound in tertiary structure of many proteins can be precipitated by phosphate anion or carbonate anion. Such processes are detrimental to the protein, because (a) they deprive the protein of the essential metal ion and (b) they result in formation of insoluble particles, the presence of which is unacceptable in some protein formulations, such as those for therapeutic purposes.

It is therefore essential to avoid any species in the formulation of a protein that can lead to precipitation of the metal bound in the protein structure. For example, it is essential to avoid the use of phosphate buffer or carbonate buffer in formulating a protein which binds calcium within its tertiary structure. Whilst the precipitation may not necessarily lead to loss of the protein function, even a very small degree of precipitation is not acceptable in many applications, for example pharmaceutical applications.

There is also a possibility of causing metal precipitation in formulations of proteins that are not metalloproteins, i.e. proteins that do not necessarily require presence of a metal for maintaining their native conformation or their function. This is because some metal ions may be attached to the protein structure as a result of their downstream or upstream processing. Consequently, metal ions may be bound onto the surface of the protein after the processing, which can lead to (a) more rapid aggregation of the protein and (b) precipitation of the metal ion by excipients (e.g. buffers) present in the formulation. The present invention addresses this problem.

It is important to realise that molecules of dissolved gases can also contribute to the competition for the metal binding. Although the coordination chemistry of dissolved gas-metal complexes has not been studied as thoroughly as that of other ligands there are various reports in the literature characterising a number of such complexes. Carbon dioxide-metal complexes (reviewed in Gibson D. H.: Coordination Chemistry Reviews 185-186 (1999) 335-355) are probably the best studied complexes involving a dissolved gas ligand. Apart from direct binding to a metal, carbon dioxide can also contribute to metal binding indirectly by giving rise to various carbonate species that are capable of metal-binding. This is due to the fact that in aqueous solutions carbon dioxide exists in equilibrium with carbonic acid and various carbonate anions:

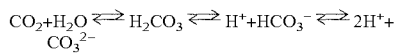

Carbonate anions are not only capable of forming complexes with metals, but in some cases can also cause their precipitation.

Oxygen is another example of a dissolved gas acting as a ligand to form dissolved gas-metal complexes. For, example, transport of oxygen by haemoglobin is facilitated by co-ordinate binding of oxygen to the iron of haeme. The oxygen molecule has four available lone pairs of electrons, some of which can be engaged in the metal binding. A number of other gases are also Lewis bases and can thus engage in co-ordinate bond formation with metal ions.

The contribution of dissolved gases to the competing for the metal may be generally underestimated for several reasons. Firstly, rather than being deliberately added to the formulation the presence of these excipients is naturally due to the equilibrium with gaseous headspace. Dissolved gases are therefore not typically listed as excipients in aqueous formulations of therapeutic proteins. Secondly, the concentration of dissolved gases in aqueous solutions is very low due to their non-polar hydrophobic nature. Thirdly, with the exception of oxygen the dissolved gases are chemically very inert, and are therefore not associated with chemical changes occurring in an aqueous formulation. Oxygen may be associated with oxidative processes, but its contribution to metal-ligand equilibria in the system has not so far been appreciated.

The solubility of gases varies considerably, and is also dependent on other parameters of the solution, such as ionic strength, temperature etc. At a constant temperature, the concentration of a given gas dissolved in a given type of liquid is directly proportional to the partial pressure of the gas which is in equilibrium with the liquid. The concentration of dissolved gas in a liquid at given temperature can be calculated from its partial pressure in equilibrium with the liquid and Henry's constant for that liquid and temperature:

$$[G] = \frac{p}{k}$$

where [G] is the concentration of dissolved gas in the liquid, p is the partial pressure and k is the henry's constant. Examples of Henry's constants for solubility of gases in water at 25° C. are:

oxygen: 769.2 (L atm)/mol
carbon dioxide: 29.4 (L atm)/mol
hydrogen: 1282.1 L (L atm)/mol
nitrogen: 1800 (L atm)/mol Thus, carbon dioxide is by far the most soluble of the above gases whilst nitrogen is the least soluble. For example, water equilibrated with a gaseous phase containing 60-fold (v/v) excess of nitrogen over carbon dioxide will contain approximately equal molar concentration of dissolved nitrogen and carbon dioxide. So, the total concentration of dissolved gases in water will be smaller if equilibrated with nitrogen atmosphere than if equilibrated with air, which, in turn, will be smaller than if in equilibrium with carbon dioxide-rich atmosphere.

One skilled in the art will understand that in order to reduce the concentration of a particular gas dissolved in a liquid phase the liquid must be packed under a headspace in which the partial pressure of the particular gas is substantially reduced. The most efficient way of reducing the total concentration of dissolved gases is by equilibrating the liquid with near-vacuum gas phase.

The hydrophobic nature of the dissolved gas molecules, such as oxygen, results in their relatively low equilibrium concentration. However, the hydrophobicity together with lack of charge and a very small size makes these excpients very mobile within the hydrophobic core of the protein molecules. Consequently, it is considerably easier for this kind of molecules to reach the metal ions within a protein structure compared with larger and charged excipients. Due to their hydrophobic nature, the molecules of dissolved gases have been shown to concentrate within the hydrophobic core of proteins. So, even though the stability constants of metal complexes with dissolved gases may be relatively low, their contribution to competing with and disrupting the co-ordinate bonds within the protein molecules increases considerably due to their ability to diffuse easily into the hydrophobic core of proteins. It is therefore important to minimise the concentration of certain dissolved gases in aqueous metalloprotein formulations in order to minimise the loss of protein structure. This is addressed in the present invention.

In addition, the diffusion and higher solubility of dissolved metals into the hydrophobic core of proteins may also disrupt various hydrophobic bonds between hydrophobic side chains of amino acids that are essential for maintaining the native three-dimensional structure. Therefore, even proteins that do not rely on appropriate binding of a metal ion in their structure may benefit from removing dissolved gases from their aqueous formulation.

The term "protein" is used herein to encompass molecules or molecular complexes consisting of a single polypeptide, molecules or molecular complexes comprising two or more polypeptides and molecules or molecular complexes comprising one or more polypeptides together with one or more non-polypeptide moieties such as prosthetic groups, cofactors etc. The invention is applicable to polypeptides of any molecular weight.

The term "polypeptide" is intended to encompass polypeptides comprising covalently linked non-amino acid moieties such as glycosylated polypeptides, lipoproteins etc.

In some aspects, the invention relates to metalloproteins, i.e. protein molecules having a particular three dimensional structure and a biological activity of interest, which activity and/or structure are dependent on retention of a particular metal ion in a binding site within the protein. The metal may be bound directly to the amino acid side chains of the protein or it can be part of a more complex chemical component which is bound within the protein structure.

In some aspects, the invention relates to proteins which are not generally considered to be metalloproteases, but binding of a particular metal ion to their structure may have an effect on the tertiary structure and/or long-term stability of the protein. Information regarding the presence of metal ions bound within the protein structures, particularly proteins of commercial interest, including the details of the metal-ligand bonds involved in the interaction can be extracted from various sources, such as the protein data bank (http://pdbbeta.rcsb.org/pdb/home/home.do).

The invention is not limited to proteins and is applicable to a wide range of biological molecules and supramolecular systems, including nucleic acids, virus-like particles and viruses. The term "supramolecular system" is used herein to encompass any system made up of a discrete number of assembled molecular subunits or components.

The term "ligand" is used herein to encompass any compound capable of binding metal ions resulting in formation of complex ions. For the purpose of this invention the ligands are divided to "weak ligands", "medium-strength ligands" and "strong ligands". The terms of "weak ligand", "medium-strength ligand" and "strong ligand" are defined based on the stability constants of their complexes with calcium ion—one of the most common metal ions found in the structure of metalloproteins, as follows: A weak ligand has a stability constant of a complex with calcium ion log K<0.5; a medium-strength ligand has stability constant of a complex with calcium ion log K between 0.5 to 2; a strong ligand has stability constant of a complex with calcium ion log K>2. All stability constants stated in this document are those measured at 25° C.

The term "displaced buffer" is used herein to encompass any additive present in a composition of specified pH which is capable of exchanging protons and has $pK_a$ value(s) at least 1 unit more or less than the pH of the composition at the intended temperature range of storage of the composition. The art of applying displaced buffers to formulations of biologicals is described in PCT/BG2007/000082.

Examples of stability constants of a selection of potential excipients in protein formulations are shown in Table 1. The table lists only a limited number of potential excipients, and the present invention is by no means limited to the use of these compounds. The stability constants of a wide range of other potential excipients can be obtained from the NIST Standard Reference Database 46.

TABLE 1

Stability constants of selcted excipients.

| Excipient | Log K |
|---|---|
| EDTA | 10.81 |
| Citrate | 3.48 |
| Histidine | 1.21 |
| Lysine | 1.05 |
| Ornithine | 1.68 |
| Methionine | 2.04 |
| Cysteine | 2.5 |
| Glutamate | 1.43 |
| Tyrosine | 1.48 |
| Aspartate | 1.7 |
| Alanine | 1.3 |
| Glycine | 1.09 |
| Glycylglycine | 1.24 |
| Malate | 2.06 |
| Phthalate | 1.6 |
| Maleate | 1.76 |
| Ascorbate | 0.2 |
| Benzoate | 0.2 |
| Salicylate | −0.87 |
| Lactate | 1.48 |
| Glycolate | 1.11 |
| TRIS | 0.25 |
| Triethanolamine | 0.87 |
| Chloride | 0.1 |
| Nitrate | 0.5 |
| Carbonate | 3.22 |
| Borate | 1.76 |
| Sulphite | 2.62 |
| Phosphate | 1.9 (in addition, calcium ion precipitates in the presence of phosphate) |

All stability constants are in relation to calcium cation ($Ca^{2+}$).

The invention is described herein using "a protein" as a representative example of a biological molecule or a supramolecular system. However, the same principles as those described herein for proteins will govern behaviour of other biological molecules with potential consequences to their stability. The invention is therefore by no means limited to proteins, but is applicable to all molecules, particularly biological molecules, whose behaviour and/or interactions with other molecules depend on binding a metal ion within their molecular structure.

Nearly all compounds that can be considered as excipients (e.g. buffers, tonicity modifiers etc.) in formulations of proteins have some degree of the ability to bind metal ions resulting in formation of complex ions. Therefore, they are likely to engage in competing for binding of metal ion(s) in the protein formulation. If such ion(s) are involved in the functional activity and/or in the three-dimensional structure of the protein the presence of such excipients will contribute to the protein instability due to causing either temporary or permanent loss of the metal from the protein structure.

Whilst it is realistically not possible to stop the competition for binding of metal ion(s) in a formulation of a protein completely, it is essential to minimise such competition in order to stabilise the protein during storage.

The competition for metal ion(s) binding in a formulation of a metalloprotein can be reduced by adding to the formulation a certain amount of the metal ion(s). The importance of the presence of the metal ion in the formulation of a some proteins is generally appreciated, and some formulations of commercially important proteins contain metal ion(s), typically a calcium ion in calcium-containing proteins.

However, it is equally important to reduce the power of the ligands surrounding the protein to bind the key metal ion and thus interfere with the proper binding of the metal within the protein structure. Due to the dynamic nature of the metal-ligand equilibria every compound present in the formulation of a loprotein will have a certain degree of the ability to interfere with the metal ion binding within the protein. This ability will depend on many parameters, such as (1) the stability constant, (2) the concentration of the excipient, (3) the concentration of other species in the system, (4) temperature etc. Whilst the excipients with high stability constants will interfere with metal binding even at relatively low concentrations the ability of excipients with lower stability constants will only be pronounced at higher concentrations.

The metal-binding power of the excipients (e.g. buffers or tonicity modifiers) surrounding the protein can be minimised by (a) selecting excipients with very low stability constants (log K) and (b) by keeping their concentration to a minimum.

Some formulations require a relatively high concentration of certain species, for example for tonicity adjustment. In such cases, it is essential to use excipients with as low stability constants of complexes with the key metals as possible.

Whilst the need to avoid very strong complexing agents, i.e. compounds with extremely high stability constants (such as EDTA) in formulations of metalloproteins may be generally appreciated, the effect of ligands with considerably lower stability constant may be underestimated. However, due to the dynamic principles of the metal binding there is some probability that even a compound with relatively low stability constant will be competing for metal binding. Whilst the compounds with lower stability constant will not be as efficient as strong complexing agents in competing for the metal binding they will still contribute to the competition over a long period of time (e.g. during storage of the protein).

Therefore, in one aspect of the present invention, an aqueous composition comprises a protein or another biological molecule or supramolecular system, further characterised in that
  (i) the composition comprises one or more metal ions at a concentration between 0.01 to 20 mM, preferably between 0.05 to 10 mM, most preferably between 0.2 mM to 5 mM;
  (ii) the composition comprises other excipients, such as buffers and tonicity modifiers, all of which excipients are weak ligands;
  (iii) the composition is substantially free of excipients which are medium-strength ligands or strong ligands.

The pH of the composition may be adjusted to a required value, for example a value that ensures best heat stability of the protein during storage.

The presence of metal ions, especially metal ions that can form very strong co-ordinate bonds with side chains of amino acids, such as copper or zinc, in protein formulations can bring about protein aggregation. In addition, some metals, such as copper or iron, may catalyse oxidative processes in aqueous formulations, especially in the presence of UV light, thus further contributing to the protein degradation. Trace amounts of such metal ions are likely to be present in aqueous formulations, even if very high purity components are used. Consequently, it may be desirable to remove such metals from the protein formulation. This can be achieved by adding to the protein formulation strong complexing agents, such as EDTA. However, various proteins, especially those whose function and/or structure is dependent on a particular metal ion, may benefit from the presence of a certain metal ion in the formulation. In such cases it is important to create an optimal balance of metal ions in the formulation so that the essential metal ion is present whilst the metal-facilitated aggregation is reduced to minimum.

Such optimal balance can be achieved by adding to the formulation at the same time (1) the desirable metal ion(s) and (2) a strong complexing agent such as EDTA. It is critical, however, that the concentration of the strong complexing agent does not exceed the concentration of the metal ion. Preferably the concentration of the strong complexing agent will be less than half of the concentration of the metal ion. Simultaneous presence of the key metal and the strong complexing agent at a concentration lower than concentration of the key metal will have the following benefits:
  1. The composition contains free ions of the desirable metal which may be instrumental in maintaining the three-dimensional structure of the protein. This contributes to the stabilisation of the protein.
  2. The composition is virtually free of other metal ions that may contribute to protein aggregation.

Calcium is one of the most common metals that is essential for maintaining the three-dimensional structure of commercially important proteins. Complexes of calcium ion with side chains of amino acids are considerably less strong than complexes of other metals, such as copper or iron. Calcium ion is thus less likely to cause aggregation of proteins than the metal ions forming strong complexes. If calcium ions are added to the formulation together with a strong complexing agent then the traces of the metals such as copper or iron will be almost completely removed whilst free calcium ion will be available to ensure optimal metal-binding to the metalloprotein.

It is essential that the complexing agent added to the formulation is a very strong one, preferably EDTA. Strong stability constant of the complexing agent will ensure that (1) the trace metals are removed almost completely form the formulation and (2) no significant concentration of the complexing agent remains free in the formulation, so it cannot contribute to the competition for metal-binding within the protein.

Whilst the simultaneous presence of metal ion and a strong complexing agent in a protein formulation is particularly beneficial for proteins binding calcium ion in their structure, the invention is by no means limited to the simultaneous use of a strong complexing agent and a calcium ion. Other metal ions can be combined with a strong complexing agent in a protein formulation to achieve the same beneficial effect.

The simultaneous use of a metal ion and a strong complexing agent, such as EDTA, in a protein formulation improves stability of proteins and is counter-intuitive.

In such formulations, it is still critical to reduce the power of other ligands surrounding the protein to bind the key metal ion and thus interfere with the proper binding of the metal within the protein structure, as detailed in the first aspect of the present invention. Therefore, in a second aspect of the present invention, an aqueous composition comprises a protein, further characterised in that
  (i) the composition comprises one or more metal ions at a concentration between 0.01 to 20 mM, preferably between 0.05 to 10 mM, most preferably between 0.2 mM to 5 mM;
  (ii) the composition comprises other excipients, such as buffers and tonicity modifiers, all of which excipients are weak ligands;
  (iii) the system additionally comprises a strong complexing agent at a concentration no higher than that of the total concentration of the added metal ions, ensuring the strong complexing agent is substantially unavailable in a free form.

The preferred strong complexing agent is EDTA. The pH of the composition may be adjusted to a required value, for example a value that ensures best heat stability of the protein during storage.

The first and the second aspect of the invention are based on addition of a metal ion to protein formulation as one of several simultaneously applied measures to ensure optimal binding of a metal within a protein structure. Whilst this will typically be the best way of ensuring the stability of a protein during storage, in some cases it may be preferable not to add metal ions to the formulation, especially if such metal ions contribute to protein aggregation by forming strong co-ordinate bonds between protein molecules. In those cases it is preferable to ensure proper metal binding only by selecting appropriate non-metal excipients to ensure that the competition for binding of metal ion that is inherently part of the protein structure is kept to a minimum. This can be achieved by (a) selecting excipients with very low stability constants (log K) and (b) by keeping their concentration to a minimum.

In such formulations it may still be essential to remove trace amounts of metal ions that are not implicated in the structure of the protein to reduce possible metal-facilitated aggregation. Such trace metals may be present in the formulations as impurities of other excipients or as a result of either upstream or downstream processing of the protein, and can be removed by adding trace amounts of a strong complexing agent, such as EDTA, to the formulation so that the trace metal ions are eliminated (i.e. bound to the complexing agent) whilst no significant concentration of the complexing agent is available to interfere with the proper binding of the key metal ion within the structure of the protein. It is not possible to provide a strictly defined concentration range of the strong complexing agent that will ensure efficient removal of the trace metal ions without leaving significant portion of the complexing agent in the free form, and some iterative experimental procedure will be needed. However, the concentration is very unlikely to exceed 1 mM.

Some formulations require a relatively high concentration of certain species, for as buffers or as tonicity modifiers. In such cases it is essential to use excipients with as low stability constants of complexes with the key metals as possible.

Therefore, in a third aspect of the present invention, an aqueous composition comprises a protein, further characterised in that
  (i) the composition comprises other excipients, such as buffers and tonicity modifiers, all of which excipients are weak ligands;
  (ii) the composition is substantially free of excipients which are medium-strength ligands or strong ligands.
  (iii) optionally, the composition additionally comprises a strong complexing agent at a very low concentration, such as no higher than 1 mM, preferably no higher than 0.5 mM, most preferably no higher than 0.1 mM, this concentration being determined experimentally to ensure removal of the free form of metal ions from the formulation whilst keeping the composition substantially free of the free form of the strong ligand.

The pH of the composition may be adjusted to a required value, for example a value that ensures best heat stability of the protein during storage.

Molecules of dissolved gases can also contribute to the competition for the metal binding, given their ability to form complexes with metal ions and their ability to diffuse easily into the protein structure due to their small size and hydrophobic nature. It is therefore desirable to reduce the concentration of dissolved gases in an aqueous formulation of a protein in order to improve the storage stability. It is particularly important to reduce the concentration of carbon dioxide as its presence is most likely to contribute to the competition for metal-binding within the protein. However, other dissolved gases are also likely to have a degree of ability to bind metal ions, and complete removal of all dissolved gases is therefore the best way to eliminate the competition for metal-binding within a protein structure.

Nitrogen and oxygen are the principal components of air, nitrogen accounting for about 79% and oxygen about 21%. Carbon dioxide is present in air at considerably lower concentration—about 0.4% (v/v). However, given the different solubilities of the three gases their concentrations in dissolved form in aqueous protein formulations equilibrated with air will be quite similar.

Equilibrating aqueous protein composition with nitrogen headspace will lead to considerable reduction of total dissolved gases. In addition, this will lead to efficient removal of carbon dioxide and oxygen—gases most likely to compete for metal binding within the structure of metalloproteins. Storage under a headspace of an inert noble gas, such as argon, will result in further reduction of total dissolved gases and removal of nitrogen. However, in order to achieve an almost complete removal of all dissolved gases the aqueous formulation must be stored under near-vacuum headspace.

Partial or complete removal of dissolved gases from the aqueous compositions of proteins is an important part of the present invention. However, it is very important to combine this principle with principles disclosed in the first three aspects of the present invention in order to achieve optimal stability of a protein. Therefore, in a fourth aspect of the present invention, an aqueous composition comprises a protein, further characterised in that
  (i) the composition comprises one or more metal ions at a concentration between 0.01 to 20 mM, preferably between 0.05 to 10 mM, most preferably between 0.2 mM to 5 mM;
  (ii) the composition comprises other excipients, such as buffers and tonicity modifiers, all of which excipients are weak ligands;
  (iii) the composition is substantially free of excipients which are medium-strength ligands or strong ligands;
  (iv) the composition is stored in a sealed container with a headspace ensuring partial or substantial removal of dissolved gases, particularly the removal of carbon dioxide, for example with nitrogen headspace or with a headspace of a noble gas such as argon or with a vacuum or near-vacuum headspace.

In a fifth aspect of the present invention, an aqueous composition comprises a protein, further characterised in that
  (i) the composition comprises one or more metal ions at a concentration between 0.01 to 20 mM, preferably between 0.05 to 10 mM, most preferably between 0.2 mM to 5 mM;
  (ii) the composition comprises other excipients, such as buffers and tonicity modifiers, all of which excipients are weak ligands;
  (iii) the system additionally comprises a strong complexing agent at a concentration no higher than that of the total concentration of the added metal ions, ensuring the strong complexing agent is substantially unavailable in a free form;
  (iv) the composition is stored in a sealed container with a headspace ensuring partial or substantial removal of dissolved gases, particularly the removal of carbon dioxide, for example with nitrogen headspace or with a headspace of a noble gas such as argon or with a vacuum or near-vacuum headspace.

In a sixth aspect of the present invention, an aqueous composition comprises a protein, further characterised in that
(i) the composition comprises excipients, such as buffers and tonicity modifiers, all of which excipients are weak ligands;
(ii) the composition is substantially free of excipients which are medium-strength ligands or strong ligands.
(iii) the composition additionally comprises a strong complexing agent at a very low concentration, such as no higher than 1 mM, preferably no higher than 0.5 mM, most preferably no higher than 0.1 mM, this concentration being determined experimentally to ensure removal of metal ions from the formulation whilst keeping the composition substantially free form of the free form of the strong ligand;
(iv) the composition is stored in a sealed container with a headspace ensuring partial or substantial removal of dissolved gases, particularly the removal of carbon dioxide, for example with nitrogen headspace or with a headspace of a noble gas such as argon or with a vacuum or near-vacuum headspace.

Preferred compositions according to the present invention comprise a protein or other biological molecule or supramolecular system and a buffer system based on salicylate ion or benzoate ion or TRIS or any combinations thereof. The composition may optionally comprise any of the following: (1) a source of a metal ion such as calcium ion, (2) a strong complexing agent, such as EDTA, at a concentration no higher than that of the total concentration of the added metal ions, (3) a source of chloride, for example in the form of sodium chloride, to adjust the ionic strength, (4) a sugar, such as sucrose or mannose, or a polalcohol, such as propyleneglycol or mannitol, (5) a surfactant, such as Polysorbate 80 or Poloxamer 188.

The following Examples illustrate the invention:

Example 1

Anthrax Recombinant Protective Antigen (rPA)

The recombinant Anthrax protective antigen was obtained from Health Protection Agency (Porton Down, UK). The stability of the protein was assayed using the following reversed-phase chromatographic procedure: Mobile phase consisted of (A) 0.1% TFA in water and (B) 0.1% TFA in 95% Propan-2-ol+5% water. Gradient elution from 30% B to 55% B over 25 mins was employed. The liquid chromatograph (Agilent 1100 series) was equipped with a 214 nm detector, guard column (Phenomenex KJO-4282) and a 4.6×250 mm column (Phenomenex Jupiter C4 300A column, 250×4.6 mm) maintained at 45° C. The flow rate was maintained at 0.5 mL min$^{-1}$. Typical sample loading was 15 µL of aqueous sample containing 0.5 mg mL$^{-1}$ rPA. Recovery was expressed as the percentage of the area of the peak corresponding to the intact rPA measured after incubation at 25° C. for a given period of time with respect to that measured prior to the storage trial. The recovery of rPA structural integrity was measured following incubation both at 37° C. and at 25° C. at pH 8.5 This pH was shown in preliminary experiments to be optimal for storage of aqueous rPA at temperatures between 25-37° C.

Anthrax rPA is known to contain calcium cations bound within its tertiary structure. The effect of excipients/buffers with various stability constants (log K) of complexes with metal ions was studied on the stability of aqueous rPA. The excipients and their stability constants (log K) with calcium ions were as follows: TRIS (log K=0.25), lysine (log K=1.4), citrate (log K=3.5), borate (log K=1.76), phosphate (log K=1.9 in addition to slow precipitation of calcium ion). All rPA samples were studied at pH about 8.5. This pH was shown in preliminary experiments to be optimal for storage of aqueous rPA.

The presence of calcium ions was found essential to ensure structural stability of rPA. However, the structural stability was also dependent on the stability constants (with respect to calcium binding) of other excipients/buffers present in the composition. So, the best stability was observed either in the absence of other excipients (i.e. in a formulation comprising only calcium chloride whilst adjusting the pH to about 8.5 by sodium hydroxide) or in the presence of an excipient with very low stability constant (TRIS). The formulation in the presence of TRIS appeared to be more stable, probably due to better pH stability compared with the calcium-only formulation. The beneficial effect of the TRIS/calcium combination was completely removed in the presence of citrate, i.e. an excipient with high stability constant. TRIS was also the only excipient/buffer that ensured improved stability in the absence of calcium. This could be due to minimal interference with calcium bonds within the rPA molecule. The presence of lysine, i.e. a compound with higher stability constant than TRIS also resulted in improved stability of rPA, although not as good as that in the presence of TRIS or in the absence of any excipients. The presence of other excipients/buffers with high stability constants (citrate, borate) was detrimental to stability of rPA.

TABLE 2

Recovery (%) of rPA structural integrity as measured by RP-HPLC in aqueous solutions following incubation at 25° C. or 37° C. for 12 weeks.

| Composition | 25° C. (12 weeks) | 37° C. (12 weeks) |
|---|---|---|
| sodium phosphate (5 mM) | <5 | <5 |
| sodium phosphate (5 mM) + calcium chloride (4 mM) | <5 | <5 |
| sodium phosphate (25 mM) | <5 | <5 |
| sodium phosphate (25 mM) + calcium chloride (4 mM) | <5 | <5 |
| TRIS (5 mM) | 36.1 | 30.7 |
| TRIS (25 mM) | <5 | <5 |
| TRIS (5 mM) + calcium chloride (4 mM) | 89.9 | 58.2 |
| TRIS (5 mM) + calcium chloride (4 mM) + citrate (20 mM) | <5 | <5 |
| citrate (20 mM) | <5 | <5 |
| lysine (5 mM) | <5 | <5 |
| lysine (5 mM) + calcium chloride (4 mM) | 32.2 | 10.2 |
| borate (5 mM) | <5 | <5 |
| borate (5 mM) + calcium chloride (4 mM) | <5 | <5 |
| calcium chloride (10 mM) | 69.9 | 41.6 |

All samples were adjusted to pH 8.5.

Example 2

Catalase (Bovine Liver)

Catalase was obtained from Sigma and was formulated in aqueous compositions at 100 µg mL$^{-1}$. The catalase solutions, both fresh and after incubation at specified temperature, were assayed for catalase activity. This was performed according to the following procedure: 2 mL of hydrogen peroxide (30 mM in water) was added to 18 mL of PBS in a 125 mL polypropylene pot. 100 μL of the catalase sample was added and mixed. The resulting mixture was incubated at room temperature precisely for 30 min. In the meantime, the following reagents were mixed in a plastic cuvette for spectrophotometric measurements:

2.73 mL of citrate/phosphate buffer (0.1 M, pH 5.0)

100 μL of TMB (3 mg/mL, dissolved in DMSO)

100 μL of lactoperoxidase

Following the 30 min incubation period, 70 μL of the catalase containing mixture was added to the cuvette, mixed and absorbance was read in approximately 30 s. The results were expressed as percentage recovery, by reference to the absorbance measured in the fresh samples (i.e. prior to incubation at increased temperature). The recovery of catalase activity was measured following incubation at 25° C. for 23 and 51 days at pH 6.8. This pH was shown in preliminary experiments to be optimal for storage of aqueous catalase.

Catalase is known to contain haem and calcium cations in its tertiary structure. The effect of excipients with various stability constants (log K) of complexes with metal ions was studied on the stability of aqueous catalase. The excipients and their stability constants (log K) with calcium ions were as follows: 25 mM TRIS (log K=0.25), 25 mM purine (log K=1.2), 25 mM lysine (log K=1.4), 25 mM citrate (log K=3.5) and 25 mM phosphate (log K=1.9 in addition to slow precipitation of calcium ion). All catalase samples studied contained 5 mM TRIS and 200 mM sodium chloride as a background solution. All samples were kept in sealed glass vials with either air or nitrogen or vacuum headspace.

The recovery of catalase activity in samples containing these ligands was dependent on the stability constants of these ligands with respect to binding metal ions. So, the recovery was considerably higher in the presence of TRIS (25 mM) then in the presence of lysine (25 mM) or purine (25 mM). The recovery was extremely low in the presence of citrate and phosphate, i.e. ligands with strong binding of calcium ions; see Table 3. For example, the catalase activity recovery following incubation at 25° C. for 23 days was <15% in the presence of either citrate or phosphate, but >25% in the presence of purine or lysine and >85% in the presence of TRIS only. After 51 days of incubation at 25° C.<4% of residual activity was observed in all samples apart form the sample containing TRIS only, which retained more than 50% of the original activity. Importantly, the recovery was further increased if the samples were kept under nitrogen headspace and particularly under a vacuum headspace (Table 3). This effect was particularly marked in the case of TRIS only, i.e. an excipient with minimal complexing ability of metal ions.

TABLE 3

Recovery of catalase activity (%) following incubation at 25° C. for 23 and 51 days in aqueous samples kept under air, nitrogen and vacuum headspace.

| | Lysine (25 mM) | Purine (25 mM) | TRIS (25 mM) | Citrate (25 mM) | Phosphate (25 mM) |
|---|---|---|---|---|---|
| 23 Days | | | | | |
| Air | 32.2 | 29.4 | 88.0 | 7.0 | 11.6 |
| Nitrogen | 40.3 | 58.0 | 100.1 | Not studied | Not studied |
| Vacuum | 49.6 | 74.5 | 100.9 | Not studied | Not studied |
| 51 Days | | | | | |
| Air | 1.8 | 3.6 | 56.3 | <1 | <1 |
| Nitrogen | 4.5 | 4.1 | 63.9 | Not studied | Not studied |
| Vacuum | 4.0 | 19.2 | 99.9 | Not studied | Not studied |

All samples were adjusted to pH 6.8 and contained 200 mM sodium chloride and 5 mM TRIS buffer.

Example 3

Horseradish Peroxidase

Horseradish peroxidase was obtained from Sigma and was formulated in aqueous compositions at 100 μg mL$^{-1}$. The horseradish peroxidase solutions, both fresh and after incubation at increased temperature, were assayed for horseradish peroxidase activity. This was performed according to the following procedure: 10 μL of the horseradish peroxidase sample was added to a cuvette containing the mixture of the following reagents:

2.5 mL of citrate/phosphate buffer (0.05 M, pH 5.0)

100 μL of hydrogen peroxide (2 mM)

100 μL of TMB (3 mg/mL, dissolved in DMSO)

These were mixed together quickly. Time=0 was counted from the addition of the horseradish peroxidase sample. Precisely after 3 min, the absorbance was then read at 630 nm. The results were expressed as percentage recovery, by reference to the absorbance measured in the samples prior to their incubation at increased temperature. The recovery of horseradish peroxidase activity was measured following incubation at both 25° C. and 40° C. for 6 weeks at pH 7. This pH was shown in preliminary experiments to be optimal for storage of aqueous horseradish peroxide at 40° C.

Horseradish peroxidase is known to contain haem and calcium cations bound within its tertiary structure. The effect of excipients with various stability constants (log K) of complexes with metal ions was studied on the stability of aqueous horseradish peroxide. The stability was studied in the following compositions:

sodium phosphate (5 mM)

sodium phosphate (5 mM)+calcium chloride (3 mM)

sodium phosphate (25 mM)

sodium phosphate (25 mM)+calcium chloride (3 mM)

TRIS (50 mM)

TRIS (50 mM)+calcium chloride (3 mM)

TRIS (5 mM)

TRIS (5 mM)+calcium chloride (3 mM)

sodium malate (5 mM)

sodium malate (5 mM)+calcium chloride (3 mM)

potassium benzoate (5 mM)+TRIS (5 mM)

potassium benzoate (5 mM)+TRIS (5 mM)+calcium chloride (3 mM)

All samples contained 100 mM sodium chloride and 0.005% (w/w) Tween 80 as a background solution. The stability constants (log K) of complexes with calcium ions of the excipients used are as follows: 0.2 (benzoate anion), 0.25

(TRIS), 1.9 (phosphate), 2.06 (malate). In addition to forming a complex with calcium ion phosphate causes its slow precipitation at neutral pH.

The recovery of horseradish peroxidase activity in samples containing these ligands was dependent on the stability constants of these ligands with respect to binding metal ions. So, the recovery was considerably higher in the presence of TRIS (5 mM) and TRIS (5 mM)/potassium benzoate (5 mM) mixture then in the presence of phosphate (5 mM or 25 mM) or malate (5 mM), i.e. ligands with strong binding of calcium ions; see Table 4. The co-presence of calcium ions in the formulation did not have a significant effect in formulations comprising only the weak ligands (TRIS or potassium benzoate), but did lead to slightly improved recovery in the presence of stronger ligands. This can be explained by the reduced effect of the strong ligands in competing for the metal ion in the presence of additional source of the metal ions.

TABLE 4

Recovery (%) of horseradish peroxidase activity in aqueous solutions following incubation at 40° C. or 25° C. for 6 weeks.

| Composition | 40° C. (6 weeks) | 25° C. (6 weeks) |
|---|---|---|
| sodium phosphate (5 mM) | 54.7 | 11.3 |
| sodium phosphate (5 mM) + calcium chloride (3 mM) | 75.6 | 25.0 |
| sodium phosphate (25 mM) | 53.6 | 10.1 |
| sodium phosphate (25 mM) + calcium chloride (3 mM) | 55.4 | 36.3 |
| sodium malate (5 mM) | 42.8 | 21.8 |
| sodium malate (5 mM) + calcium chloride (3 mM) | 58.6 | 33.9 |
| TRIS (50 mM) | 78.4 | 65.1 |
| TRIS (50 mM) + calcium chloride (3 mM) | 84.1 | 69.7 |
| TRIS (5 mM) | 97.3 | 93.6 |
| TRIS (5 mM) + calcium chloride (3 mM) | 98.1 | 96.0 |
| potassium benzoate (5 mM) + TRIS (5 mM) | 98.2 | 95.4 |
| potassium benzoate (5 mM) + TRIS (5 mM) + calcium chloride (3 mM) | 99.6 | 99.2 |

All samples were adjusted to pH 7 and contained 100 mM sodium chloride and 0.005% (w/w) Tween 80.

Example 4

Coagulation Factor VIII

The activity of Factor VIII was assayed by measuring the coagulation time in the APTT test, using CA-50 coagulometer (Sysmex). The recovery of Factor VIII coagulation activity was measured following incubation at 25° C. or 37° C. All compositions of Factor VIII were tested at pH between 6 to 6.5—the optimal pH range for stability. All compositions contained 500 mM sodium chloride, 5 mM calcium chloride and 0.005% (w/w) Tween 80.

Factor VIII is known to contain calcium cations and cations of other divalent metals in its tertiary structure. The effect of excipients with various stability constants (log K) of complexes with calcium was studied on the stability of aqueous Factor VIII. The excipients and their stability constants (log K) of complexes with calcium ions were as follows: TRIS (log K=0.25), potassium benzoate (log K=0.20), malate (log K=2.06) and triethanolamine (log K=1.4). Samples were kept in sealed glass vials with either air or nitrogen or vacuum headspace. The recovery of Factor VIII activity in samples containing these ligands was dependent on their stability constants with respect to binding metal ions. So, the coagulation activity, both at 25° C. and 37° C., was highest in the presence of a buffer system consisting of TRIS (10 mM) and potassium benzoate (10 mM). The activity recovery in the presence of other buffering systems reflected their stability constants, decreasing in the following order: triethanolamine (10 mM), histidine (10 mM) and malate (10 mM); see Table 5. Importantly, the recovery was further increased if the samples were kept under nitrogen headspace and particularly under a vacuum headspace (Table 5).

TABLE 5

Coagulation time (in seconds) of Factor VIII compositions following incubation at 25° C. or 37° C. for 4 weeks in aqueous samples kept under air, nitrogen and vacuum headspace.

| | TRIS (10 mM)/ benzoate (10 mM) | Triethanolamine (10 mM) | Histidine (10 mM) | Malate (10 mM) |
|---|---|---|---|---|
| 25° C. | | | | |
| Air | 50.8 | 53.2 | 55.8 | 62.7 |
| Nitrogen | 47.6 | 49.2 | 52.3 | 57.8 |
| Vacuum | 46.2 | Not studied | 49.2 | Not studied |
| 37° C. | | | | |
| Air | 54.3 | 58.1 | 67.5 | 75.8 |

All samples were adjusted to pH 6.5 and contained 500 mM sodium chloride, 5 mM calcium chloride and 0.005% (w/w) Tween 80. (Lower coagulation time indicates better stability of Factor VIII)

The invention claimed is:

1. An aqueous composition comprising:
   (i) a metalloprotein whose biological activity or three dimensional structure is dependent on retention of calcium ions in a binding site within the protein;
   (ii) calcium ions at a concentration of 0.01 to 20 mM;
   (iii) weak ligand buffers TRIS and benzoate, each having a stability constant measured at 25° C. for a complex with calcium ion log K<0.5; and
   (iv) a tonicity modifier which is a weak ligand having a stability constant measured at 25° C. for a complex with calcium ion log K<0.5;
   wherein said composition is substantially free of excipients which are medium-strength ligands having a stability constant measured at 25° C. for a complex with calcium ion log K between 0.5 and 2, and is substantially free of excipients in free form which are strong ligands having a stability constant measured at 25° C. for a complex with calcium ion log K>2.

2. The composition according to claim 1, which comprises an excipient that is a strong ligand having a stability constant measured at 25° C. for a complex with calcium ion log K>2 at a concentration no higher than the concentration of the calcium ions of (ii).

3. The composition according to claim 2, wherein the concentration of the excipient that is a strong ligand is <1 mM.

4. The composition according to claim 3, wherein the concentration of the excipient that is a strong ligand is <0.1 mM.

5. The composition according to claim 2, wherein the excipient that is a strong ligand is EDTA.

6. The composition according to claim 1, wherein the concentration of the calcium ions of (ii) is 0.05 to 10 mM.

7. The composition according to claim 6, wherein the concentration of the calcium ions of (ii) is 0.2 to 5 mM.

8. The composition according to claim 1, which comprises a polyalcohol or a sugar.

9. The composition of claim 1 having a pH of about 8, wherein the metalloprotein is Anthrax recombinant protective antigen and the calcium ions of (ii) are at a concentration of 1 to 20 mM.

10. The aqueous composition of claim 1 having a pH of about 6.8, wherein the metalloprotein is catalase, the calcium ions of (ii) are at a concentration of 1 to 20 mM, and the tonicity modifier is sodium chloride at a concentration of 50 to 500 mM.

11. The composition of claim 1 having a pH of about 7, wherein the metalloprotein is horseradish peroxidase, the calcium ions of (ii) are at a concentration of 1 to 20 mM, and the tonicity modifier is sodium chloride at a concentration of 50 mM to 1 M.

12. The composition of claim 1 having a pH of about 6.5, wherein the metalloprotein is blood coagulation factor VIII, the calcium ions of (ii) are at a concentration of 1 to 20 mM, the tonicity modifier is sodium chloride at a concentration of 50 mM to 1 M, and wherein the composition further comprises polysorbate 80.

13. The composition according to claim 1, wherein the tonicity modifier is sodium chloride.

14. The composition according to claim 13, wherein the sodium chloride is at a concentration of 50 mM to 1 M.

15. The composition according to claim 1, which comprises a surfactant.

16. The composition according to claim 15, wherein the surfactant is polysorbate 80.

17. The composition according to claim 1, which is in a container.

18. The composition according to claim 17, which is in a sealed container.

19. The composition according to claim 18, which is in a sealed container with a nitrogen or noble gas head space.

20. The composition according to claim 18, which is in a sealed container with a vacuum head space.

21. The composition according to claim 17, which is in an unsealed container.

* * * * *